United States Patent [19]

Danielson et al.

[11] Patent Number: 4,752,568

[45] Date of Patent: Jun. 21, 1988

[54] LABELED HYDANTOIN CONJUGATE AND ITS USE IN ANALYTICAL ELEMENT AND IMMUNOASSAYS

[75] Inventors: Susan J. Danielson; Robert J. Olyslager, both of Rochester; Michael W. Sundberg, Penfield, all of N.Y.

[73] Assignee: Eastman Kodak Company, Rochester, N.Y.

[21] Appl. No.: 818,303

[22] Filed: Jan. 13, 1986

[51] Int. Cl.[4] ........................ G01N 33/53; G01N 1/48; G01N 33/566; G01N 33/543; G01N 33/544; G01N 21/77; C12N 9/96; C07D 235/30

[52] U.S. Cl. ........................................ 435/7; 435/188; 435/805; 436/501; 436/523; 436/528; 436/170; 436/816; 422/56; 548/308

[58] Field of Search ........................... 435/7, 188, 805; 436/523, 528, 816, 170, 501; 422/56; 548/308

[56] References Cited

U.S. PATENT DOCUMENTS

| | | | |
|---|---|---|---|
| 3,875,011 | 4/1975 | Rubenstein et al. | 195/99 |
| 3,966,556 | 6/1976 | Rubenstein et al. | 195/63 |
| 3,995,021 | 11/1976 | Gross | 424/1.5 |
| 4,092,479 | 5/1978 | Parsons Jr. et al. | 548/312 |
| 4,182,856 | 1/1980 | Buckler | 536/4 |
| 4,205,952 | 6/1980 | Cais | 436/518 |
| 4,255,566 | 3/1981 | Carrico et al. | 536/27 |
| 4,404,366 | 9/1983 | Boguslaski et al. | 536/18.1 |
| 4,670,381 | 6/1987 | Frickey et al. | 435/7 |

*Primary Examiner*—Esther M. Kepplinger
*Assistant Examiner*—Carol A. Spiegel
*Attorney, Agent, or Firm*—J. Lanny Tucker

[57] ABSTRACT

A heterogeneous, competitive binding immunoassay for either phenytoin or phenobarbital is conducted with a labeled conjugate comprising a derivative of hydantoin and a label. The hydantoin derivative is 5-ethyl,5-phenyl hydantoin and it is linked to the label (e.g. an enzyme) with a linkage derived from an aliphatic monocarboxylic acid. The immunoassay can be carried out either in solution or with a dry analytical element.

20 Claims, No Drawings

LABELED HYDANTOIN CONJUGATE AND ITS USE IN ANALYTICAL ELEMENT AND IMMUNOASSAYS

FIELD OF THE INVENTION

This invention relates to clinical chemistry and to a heterogeneous, competitive binding immunoassay for the determination of either phenytoin or phenobarbital. This invention is particularly useful for the determination of these drugs in aqueous liquids, such as biological fluids.

BACKGROUND OF THE INVENTION

Competitive binding immunoassays, which take advantage of natural immunological reactions, have found widespread use as analytical techniques in clinical chemistry. Because of the specificity of the reactions, they are particularly advantageous in quantifying biological analytes which are present in very low concentration and cannot be adequately quantitated by chemical techniques. Such analytes include, for example, therapeutic drugs, narcotics, enzymes, hormones, proteins, etc.

In competitive binding assays, a labeled analyte is placed in competition with unlabeled analyte for reaction with a fixed amount of the appropriate antibody. Unknown concentrations of the analyte can be determined from the measured signal of either the bound or unbound (i.e. free) labeled analyte.

Phenytoin and phenobarbital are two drugs which are of interest today in the treatment of seizure disorders, and accurate measurement of these drugs in body fluids is important. Generally, assays for these drugs are competitive binding immunossays involving the use of a labeled analog of the drug. That is, in an assay for phenytoin, a labeled analog of phenytoin is generally placed in competition with phenytoin for a fixed amount of antibodies to phenytoin. In an assay for phenobarbital, a labeled analog of phenobarbital is generally placed in competition with the phenobarbital for a fixed amount of antibodies to phenobarbital.

It was observed, however, that under some conditions, close structural analogs of the drugs produce assays which exhibit insufficient sensitivity or dynamic range for relatively low concentrations of phenytoin or phenobarbital.

SUMMARY OF THE INVENTION

Increased sensitivity and improved dynamic range are attained in phenytoin and phenobarbital assays with the use of a labeled 5-ethyl, 5-phenyl-hydantoin conjugate wherein the label is linked to the 3-nitrogen position of the hydantoin ring with a linkage derived from an aliphatic monocarboxylic acid having from 2 to 12 carbon atoms.

This conjugate can be used in a buffered aqueous solution in carrying out a solution immunoassay for either phenytoin or phenobarbital.

This invention also provides an analytical element for the determination of phenytoin or phenobarbital comprising an absorbent carrier material and containing a labeled 5-ethyl, 5-phenyl-hydantoin conjugate wherein the label is linked to the 3-nitrogen position of the hydantoin ring with a linkage derived from an aliphatic monocarboxylic acid having from 2 to 12 carbon atoms.

Further, a method for the determination of either phenytoin or phenobarbital comprises the steps of:

A. in the presence of antibodies to either phenytoin or phenobarbital, contacting a sample of a liquid suspected of containing, respectively, either phenytoin or phenobarbital with a labeled 5-ethyl,5-phenyl-hydantoin conjugate wherein the label is linked to the 3-nitrogen position of the hydantoin ring with a linkage derived from an aliphatic monocarboxylic acid having from 2 to 12 carbon atoms, such contacting carried out in such a manner as to form a respective complex of antibodies and conjugate, and B. determining the amount of phenytoin or phenobarbital, respectively, as a result of the presence of the respective complex.

The conjugate of the present invention provides improved sensitivity and greater dynamic range for phenytoin and phenobarbital assays. Sensitivity refers to the midpoint of a dose response curve, and improved sensitivity refers to a shift of that midpoint to a lower drug concentration. The dynamic range is the total change observed in the response variable over the range of concentration of the drug tested. An improved dynamic range refers to a greater observed total change.

These improvements are achieved due to the use of a particular hydantoin derivative in the labeled analog. This analog has a particular linkage for attaching the drug moiety to the label. The useful derivative is 5-ethyl,5-phenyl-hydantoin and the linkage is derived from an aliphatic monocarboxylic acid having from 2 to 12 carbon atoms.

DETAILED DESCRIPTION OF THE INVENTION

The present invention is a specific binding assay, e.g. immunoassay, to determine either phenytoin or phenobarbital. The present invention can be used to advantage to determine these drugs in a liquid, such as a human or animal biological fluid (e.g., whole blood, serum, plasma, urine, spinal fluid, suspensions of human or animal tissue, feces, saliva, lymphatic fluid and the like). The drugs can be determined at concentrations as low as about $10^{-8}$ molar, and most generally at a concentration of from about $10^{-7}$ to about $10^{-3}$ molar.

The conjugate of this invention is formed by covalently binding a label, e.g. an enzyme, such as glucose oxidase, peroxidase, galactose oxidase, alkaline phosphatase, and others known in the art, to the hydantoin derivative described below. Fluorescent species can also be used as labels. Such species include fluorescent dyes (e.g. coumarins, umbelliferones, etc.) and fluorescent chelates, such as those described in U.S. Pat. No. 4,259,313 (issued Mar. 31, 1981 to Frank et al). Preferably, the label is an enzyme, such as glucose oxidase.

The hydantoin derivative used to make the conjugate of this invention is 5-ethyl,5-phenylhydantoin. The label is attached to the hydantoin derivative at its nitrogen in the 3-position of the hydantoin ring with a linkage derived from a straight or branched-chain, saturated or unsaturated aliphatic monocarboxylic acid having from 2 to 12 carbon atoms, e.g. acetic acid, propionic acid, butyric acid, w-valeric acid, heptanoic acid, methylacetic acid, lauric acid, and the like. Preferably, the linkage is derived from those acids having 2 to 7 carbon atoms.

The 5-ethyl,5-phenyl-hydantoin-w-valeric acid hapten used to prepare the conjugate of Example 1 below was obtained from a reaction of 5-bromo-methyl valerate and 5-ethyl,5-phenyl-hydantoin after hydrolysis of the resulting ester. The 5-ethyl,5-phenylhydantoin derivative was prepared by a known procedure. The 5-ethyl5-phenyl-hydantoin-w-valeric acid compound was then coupled to an amine attached to a label by the mixed anhydride procedure, generating amide bonds.

In the practice of this invention, the labeled conjugate allows one to determine the amount of unknown drug (e.g. phenytoin or phenobarbital) in a liquid sample. Either the bound (i.e. complexed) or unbound (i.e. uncomplexed) fraction of the labeled conjugate can be measured. Physical separation of bound and unbound conjugate, if desired, can be carried out using any suitable separation technique. In using the analytical elements described below, separation can be either vertical or horizontal or both.

The immunoassay of this invention can be carried out in solution or with a dry analytical element. In a solution assay, the labeled conjugate is generally present in a concentration of at least about $10^{-11}$ molar, and preferably from about $10^{-10}$ to about $10^{-7}$, molar. The corresponding antibodies are generally present in an amount of at least about $10^{-8}$ molar, and preferably from about $10^{-8}$ to about $10^{-3}$, molar. Other materials, e.g. buffers, surfactants, reagents, can be included in known amounts, if desired.

A solution assay is generally carried out by physically contacting and mixing the labeled analog, the appropriate antibodies and the sample suspected of containing analyte in a suitable container. The resulting solution can be incubated, if desired, for a suitable time up to 50° C. in order to promote the desired complexation and reactions. The sample is then evaluated by measuring the bound or unbound labeled conjugate with suitable equipment and procedures.

The immunoassay of this invention is also successfully carried out with a dry analytical element. Such an element comprises an absorbent carrier material which can be self-supporting single or multilayer test device. Alternatively and preferably, the absorbent carrier material is carried on a suitable nonporous support. More preferably, the element comprises a support having thereon an outermost porous spreading zone which has suitable porosity for accommodating a test sample (e.g. 1 to 100 μl), diluted or undiluted. Preferably, the spreading zone is isotropically porous, which property is created by interconnected spaces between the particles comprising the zone. By isotropically porous is meant that the spreading zone uniformly spreads the applied fluid throughout the zone.

In one embodiment of this invention, the spreading zone is designed such that when a liquid sample is applied to it, horizontal separation of bound and unbound materials is effected.

Useful absorbent materials for making such porous spreading zones are insoluble and maintain their structural integrity when exposed to water or biological fluids such as whole blood or serum. Useful elements can have spreading zones prepared from paper, porous particulate structures, porous polymeric films, cellulose, wood, glass fibers, woven and nonwoven fibrous fabrics (synthetic and nonsynthetic) and the like. Useful spreading zones can be prepared as described, for example, in U.S. Pat. Nos. 4,292,272 (issued Sept. 29, 1981 to Kitajima et al), 3,992,158 (issued Nov. 16, 1976 to Przybylowicz et al), 4,258,001 (issued Mar. 24, 1981 to Pierce et al) and 4,430,436 (issued Feb. 7, 1984 to Koyama et al) and Japanese patent publication No. 57(1982)-101760 (published June 24, 1982).

Particularly useful spreading zones are those having a particulate structure formed by organo-polymeric particles and a polymeric adhesive for those particles described in U.S. Pat. No. 4,258,001 (noted above).

The spreading zone can be carried on a suitable nonporous support. Such a support can be any suitable dimensionally stable, and preferably, nonporous and transparent (i.e. radiation transmissive) material which transmits electromagnetic radiation of a wavelength between about 200 and about 900 nm. A support of choice for a particular element should be compatible with the intended mode of detection (reflection, transmission or fluorescence spectroscopy). Useful support materials include polystyrene, polyesters [e.g. poly(ethylene terephthalate)], polycarbonates, cellulose esters (e.g. cellulose acetate), etc.

Preferably, the element also comprises a reagent zone containing an indicator composition. Other optional zones, e.g. subbing zones, radiation-blocking zones, etc. can be included if desired. All zones of the element are in fluid contact with each other, meaning that fluids and reagents and uncomplexed reaction products in the fluids can pass between regions of adjacent zones.

When the label used is an enzyme, the reagent zone of the element generally contains an indicator composition comprising one or more reagents dispersed in one or more synthetic or natural binder materials, such as gelatin, or other naturally-occurring colloids, homopolymers and copolymers, such as poly(acrylamide), poly(vinyl pyrrolidone), poly(N-isopropylacrylamide), poly(acrylamide-co-N-vinyl-2-pyrrolidone) and similar copolymers. The indicator composition comprises sufficient reagents to provide a detectable change when the enzyme label reacts with a substrate. Such materials are known to one skilled in the art.

The spreading zone of the element can contain the antibodies for the analyte to be determined at the time of the assay. The antibodies are generally commercially available, or they can be prepared using known starting materials and procedures. Generally, the appropriate antibodies are produced by inoculating a suitable animal with ligand to produce antibodies according to an appropriate protocol, and removing the generated antibodies from the animal. These techniques are well known in the art.

The antibodies can be immobilized in the spreading zone in a suitable manner. For example, the antibodies can be immobilized on a carrier material, such as glass beads, microorganisms, polymer beads or other particles, resins, and the like. Alternatively, a beaded spreading zone can serve as the carrier material so that the antibodies are immobilized therein without additional carrier material. The immobilized antibodies are generally present in the spreading zone at a coverage which corresponds to the molar amounts described above (i.e. for the solution assay) after the liquid sample is applied to the element. The labeled conjugate of this invention is generally present in the element at a coverage which corresponds to the molar amounts described above (i.e. for the solution assay) after the liquid sample is applied to the element.

The antibodies can be added to the spreading zone in an immobilized form, or immobilized therein just prior to or during the assay when the labeled conjugate is applied to the zone. Preferably, the antibodies are immobilized in the spreading zone during element manufacture.

The zones of the element of this invention can be regions of a single layer, or they can be superposed layers.

When carrying out this invention with an enzyme-labeled conjugate, the substrate for the enzyme label can be either present in the element e.g. in a reagent layer, or added to the element prior to, simultaneously with or subsequent to addition of the liquid sample. It is within the skill of the ordinary worker in clinical chemistry to determine a suitable substrate for a given enzyme label. The substrate can be a material which is directly acted upon by the enzyme label, or a material that is involved in a series of reactions which involve enzymatic reaction of the label. Using glucose as an example of a substrate, it is generally present in a zone of the element in an amount of at least about 0.01, and preferably from about 0.01 to about 2.5, moles/m$^2$. A worker skilled in the art would know how to adjust the amount of a particular substrate for the amount of enzyme label used in the assay.

The element can also contain an indicator composition comprising one or more reagents which provides a detectable species as a result of reaction of the enzyme label. Preferably, the indicator composition is a colorimetric indicator composition which provides a colorimetrically detectable species as a result of enzymatic reaction of an enzyme label with a substrate. The indicator composition can be a single compound which produces a detectable dye upon enzymatic reaction, or a combination of reagents which produce the dye. For example, when glucose is used as the substrate and glucose oxidase as the enzyme label, the colorimetric indicator composition can include a color coupler and oxidizable compound which react to provide a colored dye. Alternatively, the composition can include a leuco dye and peroxidase or another suitable peroxidative compound which generate a detectable dye as a result of the formation of hydrogen peroxide produced when glucose oxidase converts glucose to gluconic acid. Useful leuco dyes are known in the art and include those, for example, described in U.S. Pat. No. 4,089,747 (issued May 16, 1978 to Bruschi) and U.S. Ser. No. 612,509, filed May 21, 1984 by Babb et al. The particular amounts of the colorimetric indicator composition and its various components are within the skill of a worker in the art.

The zones of the element can contain a variety of other desirable but optional components, including surfactants, thickeners, buffers, hardeners, antioxidants, coupler solvents, and other materials known in the art. The amounts of these components are also within the skill of a worker in the art.

The immunoassay of this invention can be manual or automated. In general, the amount of a ligand in a liquid is determined by taking the element from a supply roll, chip packet or other source and physically contacting a finite area of the spreading layer with a sample of the liquid (e.g. 1 to 100 μl) so that the liquid sample mixes with the conjugate and any reagents in the element. Reagents can also be added simultaneously or sequentially with the liquid sample.

In one embodiment, contact of the sample can be accomplished in such a manner that complexation of antibodies with drug or conjugate and substantial horizontal separation of uncomplexed and complexed analyte occur during sample introduction. This contact can be carried out by hand or with a machine using a pipette or other suitable dispensing means to dispense the test sample. The sample of liquid can be applied to the element spreading layer in a number of ways to effect horizontal separation. For example, a relatively large liquid sample (e.g. up to 100 μl) can be applied slowly (e.g. over at least about 5 seconds) in a continuous manner using a pipette, capillary tube or other means. Alternatively, the sample can be applied in small portions, e.g. as a series of two or more droplets (e.g. 0.1 to 1 μl) over a period of time (e.g. over at least about 5 seconds).

In another embodiment, horizontal or vertical separation can be accomplished by slowly adding a wash fluid after the liquid sample has been applied to the element. This wash causes unbound materials (i.e. drug and labeled conjugate) to move away from the bound materials. The wash fluid can contain a buffer and any other reagents that are desired, e.g. an enzyme substrate.

If the labeled conjugate is not incorporated in the element during manufacture, it can be mixed with the test sample simultaneously with or prior to contact with the element.

After sample application in either embodiment, the element is exposed to any conditioning, such as incubation, heating or the like, that may be desirable to quicken or otherwise facilitate obtaining the test result.

The amount of either phenytoin or phenobarbital is determined by passing the element through suitable apparatus for detecting the complexed labeled conjugate directly or the detectable species formed as a result of enzymatic reaction of an enzyme label and a substrate. In an enzymatic reaction, the resulting dye is generally determined by measuring the rate of change in reflection or transmission density or fluorescence in the area of the element which was contacted with the test sample. In the embodiments involving horizontal separation, the area which is measured is the center of the contacted area, generally from about 3 to about 10 mm in diameter. Most of the complexed conjugate is in this finite area. The amount of analyte in the liquid sample is inversely proportional to the amount of label measured in the center of the finite area. Generally, label measurement is carried out after from about 5 to about 500 seconds after sample contact and spreading.

The following example is provided to illustrate the practice of the present invention. The materials used were either obtained commercially or prepared using known starting materials and preparatory procedures. The conjugate of this invention used in the example was prepared by the procedure described above.

As used in the context of this disclosure and the claims, I.U. represents the International Unit for enzyme activity defined as one I.U. being the amount of enzyme activity required to catalyze the conversion of 1 μmole of substrate per minute under standard pH and temperature conditions for the enzyme.

EXAMPLE 1:

Determination of Phenytoin

An analytical element for the determination of phenytoin was prepared having the format and components illustrated below. Phenytoin is also known as diphenylhydantoin.

| Spreading Layer | |
|---|---|
| Polystyrene Beads (5–20 μm) coated with normal rabbit | 25–180 g/m$^2$ |

-continued

| | |
|---|---|
| serum | |
| Poly(n-butyl acrylate-co-styrene-co-2-acrylamido-2-methylpropane sulfonic acid, sodium salt) [75:20:5 weight ratio] adhesive | 1-18 $g/m^2$ |
| ZONYL FSN surfactant | 0.1-2.5 $g/m^2$ |
| *S. aureus* coated with phenytoin anti-serum | 2-20 $g/m^2$ |
| Interlayer | |
| Gelatin (hardened) | 1-20 $g/m^2$ |
| ZONYL FSN surfactant | 0.1-2.5 $g/m^2$ |
| Reagent Layer | |
| Gelatin (hardened) | 2-20 $g/m^2$ |
| Leuco Dye* | 0.025-0.6 $g/m^2$ |
| 5,5-dimethyl-1,3-cyclohexanedione | 0.01-0.5 $g/m^2$ |
| Glucose | 0.9-6 $g/m^2$ |
| 4-Hydroxyacetanilide | 0.01-0.2 $g/m^2$ |
| Sodium dodecyl sulfate | 0.5-10 $g/m^2$ |
| Peroxidase | 1,000-50,000 I.U./$m^2$ |
| /Poly(ethylene terephthalate) Support/ | |

*4,5-bis(4-dimethylaminophenyl)-2-(4-hydroxy-3,5-dimethoxyphenyl)imidazole

A series of test samples containing various amounts of phenytoin were prepared in a buffered solution comprising 0.01 molar 3-(N-morpholino)-propanesulfonic acid buffer (pH 7), 0.15 molar sodium chloride and 0.05% rabbit gamma globulin. The concentrations of phenytoin in the test samples are listed in Table I below.

The following labeled conjugates were used in the tests:

Label I (Control): diphenylhydantoin-w-valerate-glucose oxidase.

Label II (Invention): 5-ethyl,5-phenylhydantoin-w-valerate-glucose oxidase.

Each label was mixed with each test sample and tested by spotting an 8 μsample of the resulting mixture on the element and incubating the element for 7 minutes at 37° C. During the incubation, reflectance densities were monitored at 670 nm using a reflectometer. The rate of change in dye density was calculated from measurements taken between 60 and 120 seconds into the incubation. The Williams-Clapper transform (*J. Optical Soc. Am.*, 43, 595, 1953 was used to determine transmission density values from reflectance density values.

The results are shown in Table I below. These data show that the observed rate, shown as the change in transmission density ($D_T$) with time, is inversely proportional to the concentration of phenytoin in the test sample. From dose response curves plotted using these data, a dynamic range of 0.076 was obtained with the Control labeled conjugate whereas the labeled conjugate of the present invention provided a dynamic range of 0.155. This indicates that a significantly greater dynamic range was obtained with the assay of the present invention.

Additionally, a 50-fold increase in sensitivity was obtained with the assay of the present invention over the assay using the Control conjugate. This increase in sensitivity was shown by a shift in the midpoint of the dose response curve for the assay of this invention to a lower drug concentration.

TABLE I

| Phenytoin Concentration (molar) | $D_T$/min. (Control) | $D_T$/min. (Invention) |
|---|---|---|
| 0 | 0.290 | 0.307 |
| $10^{-8}$ | 0.283 | 0.289 |
| $10^{-7}$ | 0.275 | 0.267 |
| $10^{-6}$ | 0.264 | 0.225 |
| $10^{-5}$ | 0.245 | 0.188 |
| $10^{-4}$ | 0.221 | 0.154 |
| $2 \times 10^{-4}$ | 0.214 | 0.152 |

The invention has been described in detail with particular reference to preferred embodiments thereof, but it will be understood that variations and modifications can be effected within the spirit and scope of the invention.

We claim:

1. A labeled 5-ethyl,5-phenyl-hydantoin conjugate wherein said label is linked to the 3-nitrogen position of said hydantoin ring with a linkage derived from an aliphatic monocarboxylic acid having from 2 to 12 carbon atoms.

2. The conjugate of claim 1 wherein said label is an enzyme.

3. The conjugate of claim 2 wherein said enzyme is glucose oxidase.

4. The conjugate of claim 1 wherein said carboxylic acid has from 2 to 7 carbon atoms.

5. A buffered aqueous solution comprising a buffer and a labeled 5-ethyl,5-phenyl-hydantoin conjugate wherein said label is linked to the 3-nitrogen position of said hydantoin ring with a linkage derived from an aliphatic monocarboxylic acid having from 2 to 12 carbon atoms.

6. The solution of claim 5 wherein said label is an enzyme and said aliphatic monocarboxylic acid has from 2 to 7 carbon atoms.

7. The solution of claim 6 wherein said enzyme is glucose oxidase.

8. An analytical element for the determination of phenytoin or phenobarbital comprising an absorbent carrier material and containing a labeled 5-ethyl,5-phenyl-hydantoin conjugate wherein said label is linked to the 3-nitrogen position of said hydantoin ring with a linkage derived from an aliphatic monocarboxylic acid having from 2 to 12 carbon atoms.

9. The element of claim 8 further comprising antibodies to either phenytoin or phenobarbital.

10. The element of claim 8 wherein said absorbent carrier material is a porous spreading zone carried on a nonporous support.

11. The element of claim 10 further comprising a reagent zone containing an indicator composition for providing a detectable change in response to the presence of either phenytoin or phenobarbital.

12. The element of claim 8 wherein said conjugate label is an enzyme and said monocarboxylic acid has from 2 to 7 carbon atoms.

13. A method for the determination of either phenytoin or phenobarbital comprising the steps of:

A. in the presence of antibodies for either phenytoin or phenobarbital, contacting a sample of a liquid suspected of containing, respectively, either phenytoin or phenobarbital with a labeled 5-ethyl,5-phenyl-hydantoin conjugate wherein said label is linked to the 3-nitrogen position of said hydantoin ring with a linkage derived from an aliphatic monocarboxylic acid having from 2 to 12 carbon atoms, such contacting carried out in such a manner as to form a respective complex of antibodies and conjugate, and B. determining the amount of phenytoin or phenobarbital, respectively, as a result of the presence of said respective complex.

14. The method of claim 13 carried out with an analytical element containing said labeled conjugate.

15. The method of claim 13 wherein said element contains said antibodies.

16. The method of claim 13 wherein said label is an enzyme and said monocarboxylic acid has from 2 to 7 carbon atoms.

17. The method of claim 13 wherein said element comprises a nonporous support having thereon a porous spreading zone.

18. The method of claim 14 wherein said liquid sample is contacted with said element in such a manner that said antibody-conjugate complex is immobilized in said element and horizontal separation of uncomplexed conjugate from immobilized complexed conjugate is effected.

19. The method of claim 18 wherein said separation is accomplished with a wash step subsequent to said contacting step.

20. The method of claim 13 wherein said conjugate is a glucose oxidase-labeled 5-ethyl,5-phenyl-hydantoin linked with a linkage derived from ω-valeric acid.

* * * * *